United States Patent
Jung et al.

(10) Patent No.: US 7,860,578 B2
(45) Date of Patent: *Dec. 28, 2010

(54) MINIATURE CIRCULAR MAPPING CATHETER

(75) Inventors: Eugene J. Jung, Nesconset, NY (US); Dong Ik Shin, Poway, CA (US); Eric Scott Vaughan, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 659 days.

This patent is subject to a terminal disclaimer.

(21) Appl. No.: 11/891,065

(22) Filed: Aug. 8, 2007

(65) Prior Publication Data

US 2009/0043368 A1 Feb. 12, 2009

(51) Int. Cl.
*A61N 1/00* (2006.01)
(52) U.S. Cl. .................................................. 607/122
(58) Field of Classification Search ................. 600/118, 600/374, 424, 431, 569, 585; 606/27, 34; 607/122, 116; 604/28, 529
See application file for complete search history.

(56) References Cited

U.S. PATENT DOCUMENTS

| | | | |
|---|---|---|---|
| 5,295,484 A | 3/1994 | Marcus et al. | |
| 5,582,609 A | 12/1996 | Swanson et al. | |
| 5,626,136 A | 5/1997 | Webster, Jr. | |
| 5,680,860 A | 10/1997 | Imran | |
| 5,860,920 A | 1/1999 | McGee et al. | |
| 5,971,983 A | 10/1999 | Lesh | |
| 6,004,269 A | 12/1999 | Crowley et al. | |
| 6,237,605 B1 | 5/2001 | Vaska et al. | |
| 6,315,778 B1 | 11/2001 | Gambale et al. | |
| 6,325,797 B1 | 12/2001 | Stewart et al. | |
| 6,605,084 B2 | 8/2003 | Acker et al. | |
| 6,628,976 B1 | 9/2003 | Fuimaono et al. | |
| 6,635,054 B2 | 10/2003 | Fjield et al. | |
| 6,645,199 B1 | 11/2003 | Jenkins et al. | |
| 6,702,811 B2 | 3/2004 | Stewart et al. | |
| 6,771,996 B2 | 8/2004 | Bowe et al. | |
| 6,808,524 B2 | 10/2004 | Lopath et al. | |
| 2002/0019627 A1* | 2/2002 | Maguire et al. | 606/27 |
| 2003/0060821 A1 | 3/2003 | Hall et al. | |
| 2003/0069578 A1 | 4/2003 | Hall et al. | |

(Continued)

FOREIGN PATENT DOCUMENTS

EP 1457225 9/2004

(Continued)

*Primary Examiner*—George Manuel
*Assistant Examiner*—Robert N Wieland
(74) *Attorney, Agent, or Firm*—Seager, Tufte & Wickhem, LLC (57) ABSTRACT

A cardiac ablation device, including a catheter and an expandable ablation element incorporating one or more balloons at the distal end of the catheter, has a continuous passageway extending through it from the proximal end of the catheter to the distal side of the expandable ablation element. A probe carrying electrodes is introduced through this passageway and deploys, under the influence of its own resilience, to a structure incorporating a loop which is automatically aligned with the axis of the expandable ablation device, so that minimal manipulation is required to place the probe. The probe may have an atraumatic tip with a ball formed at the leading edge. The atraumatic tip prevents any tissue damage such as perforation of heart wall.

40 Claims, 6 Drawing Sheets

U.S. PATENT DOCUMENTS

| | | |
|---|---|---|
| 2004/0176757 A1 | 9/2004 | Sinelnikov et al. |
| 2004/0181137 A1 | 9/2004 | Rodriguez et al. |
| 2006/0106295 A1 | 5/2006 | Jais et al. |
| 2006/0287592 A1 | 12/2006 | Rodriguez et al. |
| 2008/0249518 A1 | 10/2008 | Warnking et al. |

FOREIGN PATENT DOCUMENTS

| | | |
|---|---|---|
| WO | WO-2005102199 | 11/2005 |
| WO | WO-2006055534 | 5/2006 |

* cited by examiner

MINIATURE CIRCULAR MAPPING CATHETER

BACKGROUND ART

The present invention relates to apparatus and methods for cardiac ablation and to miniature sensor structures useful in such apparatus and methods.

Contraction or "beating" of the heart is controlled by electrical impulses generated at nodes within the heart and transmitted along conductive pathways extending within the wall of the heart. Certain diseases of the heart known as cardiac arrhythmias involve abnormal generation or conduction of the electrical impulses. One such arrhythmia is atrial fibrillation or "AF." Certain cardiac arrhythmias can be treated by deliberately damaging the tissue along a path crossing a route of abnormal conduction, either by surgically cutting the tissue or by applying energy or chemicals to the tissue, so as to form a scar. The scar blocks the abnormal conduction. For example, in treatment of AF, it has been proposed to ablate tissue in a partial or complete loop around a pulmonary vein, within the ostium or opening connecting the vein to the heart, or within the wall of the heart surrounding the ostium. It would be desirable to perform such ablation using a catheter-based device which can be advanced into the heart through the patient's circulatory system.

As described in commonly assigned U.S. Pat. No. 6,635,054, the disclosure of which is incorporated by reference herein, an expansible structure is used as a reflector for directing and focusing ultrasonic waves from an ultrasonic transducer into a region of tissue to be ablated. This arrangement can be used, for example, to treat atrial fibrillation by ablating a circular region of myocardial tissue encircling the ostium of a pulmonary vein. The ablated tissue forms a barrier to abnormal electrical impulses which can be transmitted along the pulmonary veins and, thus, isolates the myocardial tissue of the atrium from the abnormal impulses. As disclosed in commonly assigned U.S. Provisional Patent Application Ser. No. 60/448,804, filed Feb. 20, 2003, and in commonly assigned, co-pending U.S. Published Patent Application No. 2004/0176757 (hereinafter "the '757 application") and PCT International Application No. PCT/US04/05197, the disclosures of which are incorporated by reference herein, a catheter-carried expansible ablation structure as disclosed in the '054 patent can be equipped with a steering mechanism so that the orientation of the expansible structure relative to the heart can be controlled by the physician without relying upon physical engagement with the pulmonary vein or pulmonary vein ostium.

It is often desirable to monitor electrical signals propagating within the heart. For example, McGee et al., U.S. Pat. No. 5,860,920, discloses a structure incorporating an elongated element with numerous electrodes disposed along a distal region of the structure. The structure is advanced into the heart within a guide tube or sheath, which is then retracted so as to expose the distal region. In this condition, the distal region, under its own resilience, forms itself into a hoop shape, which can be pressed into engagement with a region of the heart wall as, for example, a region surrounding the bicuspid valve or the mitral valve. The electrodes pick up electrical signals propagating within the heart. The electrodes can be connected to a source of electrical energy, so that the electrical energy applied through the electrodes ablates the cardiac tissue. Swanson et al., U.S. Pat. No. 5,582,609, discloses another loop-forming structure carrying electrodes for electrical ablation. Fuimaono et al., U.S. Pat. No. 6,628,976, discloses a catheter with a similar loop-like structure said to be useful in mapping electrical activity or "wavelets" within a pulmonary vein, coronary sinus or other "tubular structure" prior to treatment of the condition.

Marcus et al., U.S. Pat. No. 5,295,484, discloses a catheter carrying both an ultrasonic transducer and electrodes for sensing electrical potentials within the heart. These electrodes can be used to allow the physician to determine whether the arrhythmia has persisted after the ablation process. Also, the aforementioned '054 patent and '054 patent disclose, in certain embodiments, expansible balloon structures having ring-like electrodes thereon for detecting electrical signals within the heart.

Despite all of these efforts in the art, however, still further improvement would be desirable. Particularly, providing sensing structures that prevent damage to the tissue and are capable of passing through a lumen smaller than one millimeter is desirable. Providing electrical sensing structures on a balloon-like or other expansible ablation device complicates fabrication of the device and makes it more difficult to make the device collapse to a small diameter for advancing or withdrawing the device through the vascular system. Further, mounting the electrodes on the same catheter as an ultrasonic transducer, as disclosed in the '484 patent, limits placement of the electrodes and the configuration of the transducer array and associated structures. The particular structures shown in the '484 patent, for example, are not well suited to formation of a ring-like lesion or sensing of electrical potentials at numerous locations. Use of a loop-forming sensing element entirely divorced from an ablation device, as contemplated in U.S. Pat. No. 6,628,976, necessarily requires separate steps for placement of such a device which adds both complexity and risk to the procedure.

SUMMARY OF THE INVENTION

One aspect of the present invention provides apparatus for cardiac treatment which includes a catheter having proximal and distal ends and a lumen, as well as an expansible ablation device mounted at or near the distal end of the catheter. The ablation device has a collapsed condition and an expanded condition, and is operative to apply energy to cardiac tissues in proximity to the device when the device is in the expanded condition. In its expanded condition, the device and catheter define a port open to the exterior of the expansible ablation device on the distal side of the device. Desirably, the ablation device defines a bore extending through the ablation device. The bore has a first end communicating with the lumen and a second end defining the port.

Apparatus according to this aspect of the invention desirably also includes an elongated sensor probe which also has proximal and distal ends. The sensor probe includes one or more electrodes disposed adjacent the distal end of the sensor probe. The lumen and the ablation device are constructed and arranged so that the sensor probe can be removably positioned in the passageway, with the distal end of the sensor probe projecting out of the ablation device through the port. The sensor probe has a distal section and a floppy section formed in the distal section. The distal most tip of the sensor probe has a ball formed thereon. The floppy section has a wire core and a polymeric tube covering the wire core. The polymeric tube is made from a soft material such as a thermoplastic elastomer or a polyether block amide and has a low durometer value, for example, 35-72 Shore D. An example of the soft material is Pebax®. The wire and the polymeric tube are in engagement in the area near the ball such that there is no relative motion between them in the area near the ball.

A further aspect of the invention provides methods of cardiac ablation which include the steps of advancing an apparatus including a catheter and an expansible ablation device into the subject while the ablation device is in a collapsed condition, until the ablation device is disposed in a chamber of the subject heart, and then expanding the ablation device to an expanded condition. In a method according to this aspect of the invention, the ablation device desirably is positioned in a desired disposition relative to the heart and actuated to apply energy in a loop-like region having a predetermined spatial relationship to the ablation device, and thereby ablate the tissue in this region so as to form a lesion. Methods according to the invention desirably further include the step of advancing a sensing probe with atraumatic tip having a floppy section with a ball formed at the leading edge, through a continuous passageway from the proximal end of the catheter through the ablation device, so that a distal region of the sensing probe projects out of a port on the ablation device and contacts tissue of the subject adjacent the ablation device. In methods according to this aspect of the invention, the ablation device desirably at least partially positions the projecting distal region of the sensing probe relative to the heart. The method desirably further includes the step of detecting electrical signals in the subject using the sensing probe. Methods according to this aspect of the invention afford advantages similar to those discussed above in connection with the apparatus.

Yet another aspect of the invention provides a probe having a proximal end and a distal end. A ball is formed at the tip of the distal end. A floppy section is attached to the ball. The floppy section has a wire core and a polymeric tube covering the wire core. The polymeric tube is made from a soft material such as Pebax®. The wire core and the polymeric tube are in engagement in the area near the ball such that there is no relative motion between them in the area near the ball. In its deployed condition, the probe body desirably is hoop shaped. The hoop desirably carries one or more of the functional elements such as the electrodes.

Yet another aspect of the invention provides a probe which includes a catheter having a proximal end and a distal end. The distal end when unconstrained form a circular loop and an arcuate stem attached to the circumference of the loop. The arcuate stem has a maximum first radius about same size as the diameter of the loop and a minimum second radius equal to about one fourth of the diameter of the loop. The first radius is measured by projecting the stem in a plane that is perpendicular to the plane of the loop and the second radius is measured by projecting the stem in the plane of the loop. The loop desirably carries one or more of the functional elements such as the electrodes.

These and other objects, features and advantages of the present invention will be more readily apparent from the detailed description of the preferred embodiments set forth below, taken in conjunction with the accompanying drawings.

DETAILED DESCRIPTION

Figure 1:
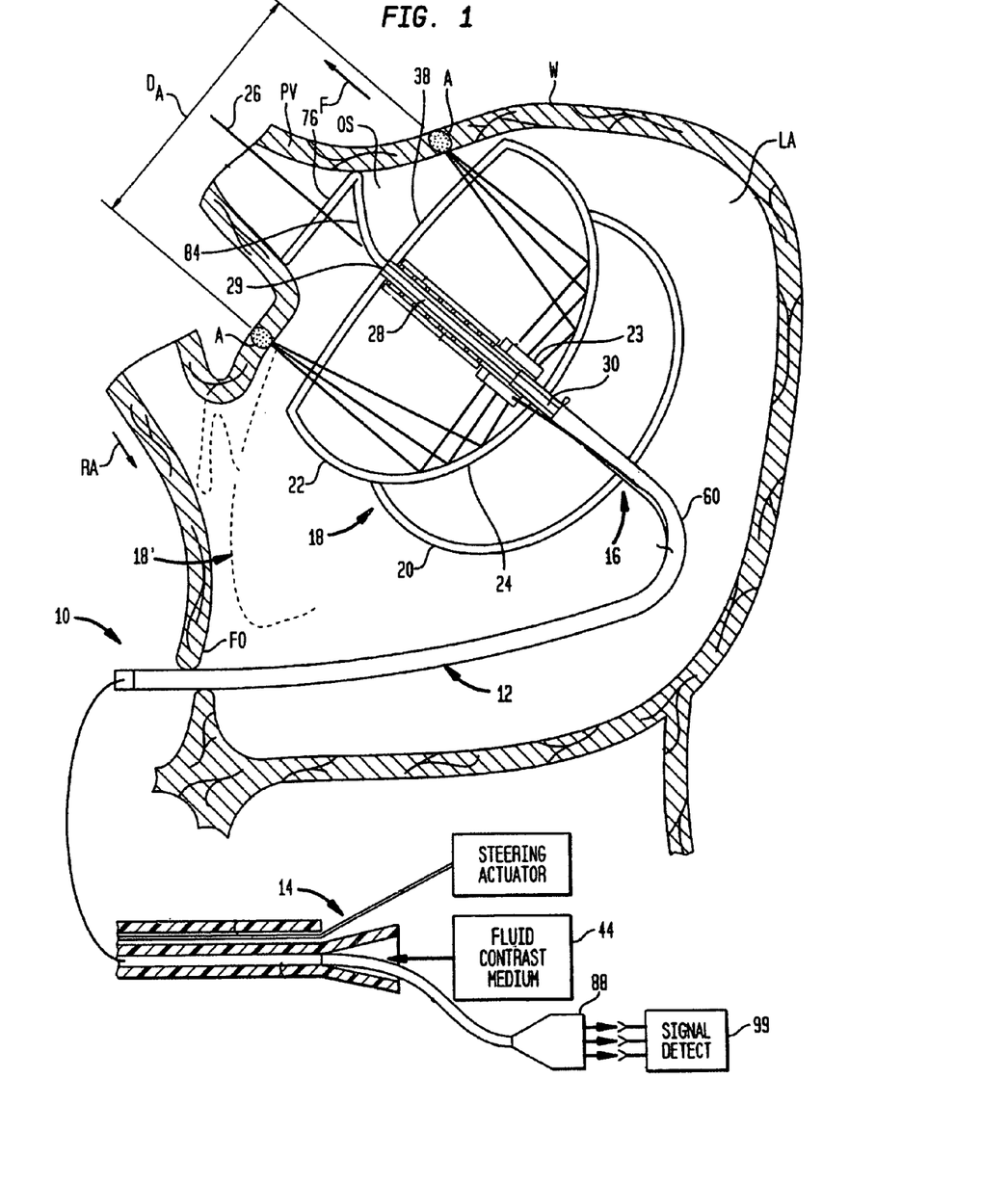
FIG. 1 is a diagrammatic, partial sectional view of apparatus in accordance with one embodiment of the invention during one stage of a method in accordance with an embodiment of the invention.

As seen in FIG. 1, apparatus according to one embodiment of the invention includes an insertable structure 10 incorporating an elongated catheter 12 having a proximal end 14, which remains outside of the body, and a distal end 16 adapted for insertion into the body of the subject. As used in this disclosure with reference to structures which are advanced into the body of a subject, the "distal" end of such a structure should be taken as the end which is inserted first into the body and which penetrates to the greatest depth within the body, whereas the proximal end is the end of the structure opposite to the distal end. Insertable structure 10 also includes an ablation unit 18 mounted to catheter 12 adjacent distal end 16. Ablation unit 18 incorporates a reflector balloon 20 and a structural balloon 22 having a common wall 24. Reflector balloon 20 is linked to an inflation lumen (not shown) in catheter 12, which extends to the proximal end of catheter 12 and which is connected, during use, to a source of a gas under pressure, such as air or, more preferably, carbon dioxide, as, for example, to a gas-filled hypodermic syringe, so that reflector balloon 20 can be inflated with a gas. Structural balloon 22 is connected through a separate inflation lumen (not shown) to a source of a liquid such as isotonic saline solution, so that structural balloon 22 can be inflated with the liquid. A cylindrical ultrasonic emitter 23 is mounted within structural balloon 22. Balloons 20 and 22, and particularly the common wall 24 separating balloons 20 and 22, are designed so that in their inflated, operative condition illustrated in FIG. 1, balloons 20 and 22 are in the form of bodies of revolution about a central or forward-to-rearward axis 26. Emitter 23 is cylindrical and is coaxial with balloons 20 and 22.

A tube defining a bore 28 extends through structural balloon 22 at central axis 26. Tube bore 28 communicates with a port 29 on or forward of a forward wall 38 of structural balloon 22. Tube bore 28 also communicates with a lumen 30 within catheter 12. Lumen 30 extends to proximal end 14 of catheter 12 and is provided with a suitable fluid connection such as a Luer hub. Tube bore 28 and lumen 30 together form a continuous passageway extending from outlet port 29, just distal to the ablation device back to proximal end 14 of catheter 12. The tube defining bore 28 may be formed from a material such as an expanded polymer of the type commonly used in vascular grafts, so that the interior bore 28 of the tube remains patent when the tube is stretched.

The common wall 24 separating balloons 20 and 22 forms an active, reflective interface. This active interface desirably has the form of a surface of revolution of a parabolic section around central axis 26. When balloons 20 and 22 are in their inflated, expanded configuration shown in FIG. 1, ultrasonic waves emitted by emitter 23 are directed radially outwardly away from axis 26 and impinge on the parabolic active interface formed by common wall 24, where it is reflected forwardly and slightly outwardly away from axis 26 and focused so that the ultrasonic waves emitted along various paths mutually reinforce within a ring-like ablation region A, just forward of forward wall 38 of structural balloon 22 encircling axis 26. The focused ultrasonic waves in this region can effectively ablate myocardial tissue and form a substantial conduction block extending through the heart wall in a relatively short time, typically about a minute or less. The ablation unit 18 can be selectively steered to position it in a desired orientation for ablating the tissue in a desired location.

Figure 2:
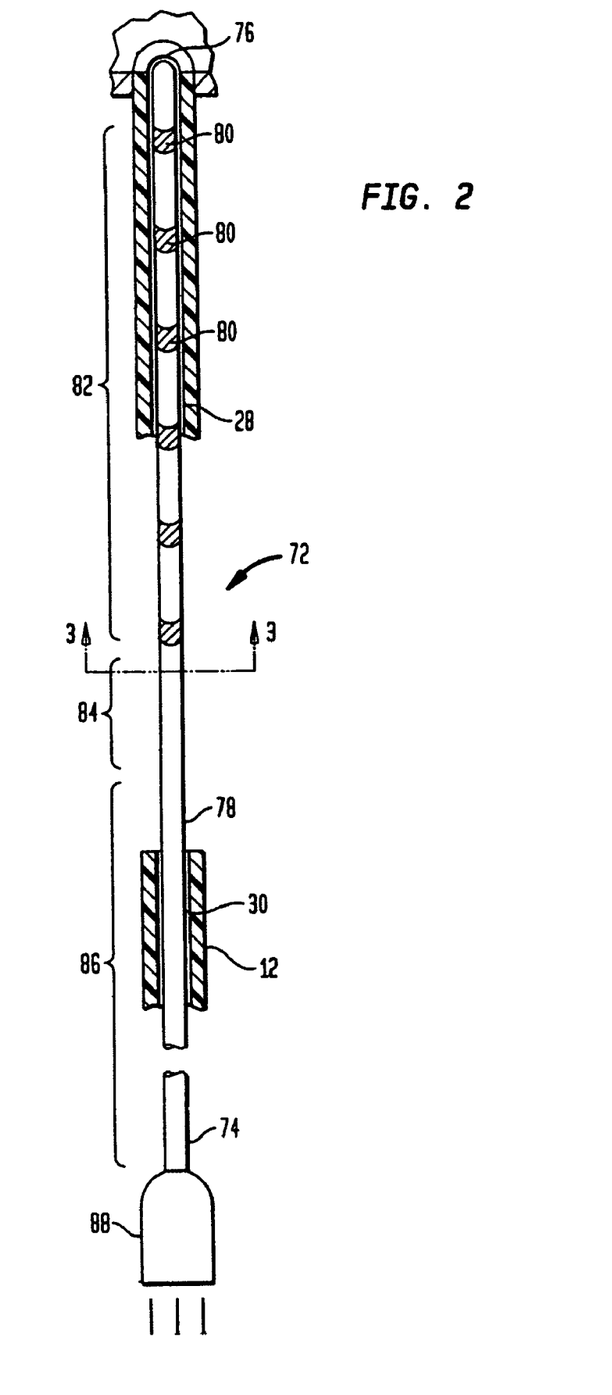
FIG. 2 is a fragmentary, diagrammatic perspective view depicting components of the apparatus shown in FIG. 1 at another stage in the method.
Figure 3:
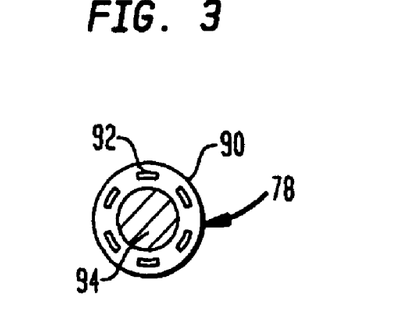
FIG. 3 is a diagrammatic sectional view taken along line 3-3 in FIG. 2.

The apparatus further includes an elongated sensor probe 72 (FIG. 2) having a proximal end 74 and a distal end 76. Probe 72 includes an elongated resilient body having a diameter smaller than the inside diameter of lumen 30. A plurality of electrodes 80 (FIGS. 2 and 4) extend around resilient probe body 78 in an operative region 82 adjacent distal end 76 of probe 72, also referred to as a "hoop region." The probe body 78 also includes a juncture region 84 disposed proximal to operative region 82 and a main or base region 86 extending from juncture region 84 to proximal end 74 of probe 72. A connector 88 is provided at proximal end 74 of probe 72. As best seen in FIG. 3, resilient body 78 includes a dielectric layer 90 and conductors 92 extending within dielectric layer 90 from electrodes 80 to connector 88 (FIG. 2). Probe body 78 also includes a resilient metallic element 94 extending along the length of probe body 78. Element 94 may be a super elastic material such as an alloy of nickel and titanium, commonly referred as nitinol. The particular arrangement depicted in FIG. 3, with conductors 92 disposed around resilient element 94, is not essential. For example, conductors 92 may be grouped to one side of elastic element 94. Probe 72 can be placed into the continuous passageway defined by the catheter lumen 30 and bore 28, and can be removed therefrom.

Figure 4:
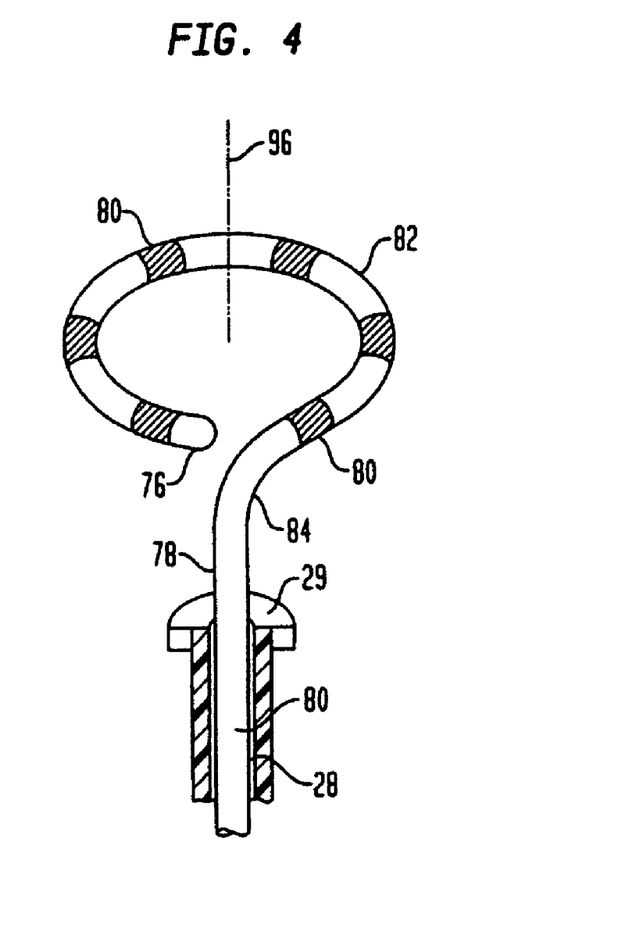
FIG. 4 is a diagrammatic perspective view of the components illustrated in FIG. 2 during another stage in the method.

In its free or unconstrained condition, resilient body 78 assumes the shape depicted in FIG. 4. In this shape, hoop region forms a generally circular hoop 82 in a plane transverse to an axis 96 defined by the distal-most part of base region 86. Hoop 82 encircles axis 96 and is substantially coaxial therewith. The connecting or transition region 84 extends outwardly from axis 96 and also slopes slightly in the forward or distal direction. As discussed below, the probe body is in this unconstrained state when deployed within the heart, and accordingly, this condition is also referred to herein as the "deployed" condition of the probe body. The distal portion of the hoop region may be of an atraumatic design similar to one shown in FIG. 10 and described in detail hereafter. In a variation of the embodiment shown in FIG. 4, the hoop region and juncture region 84 may have the shape described in detail hereafter and depicted in FIGS. 11 and 12.

Figure 5:
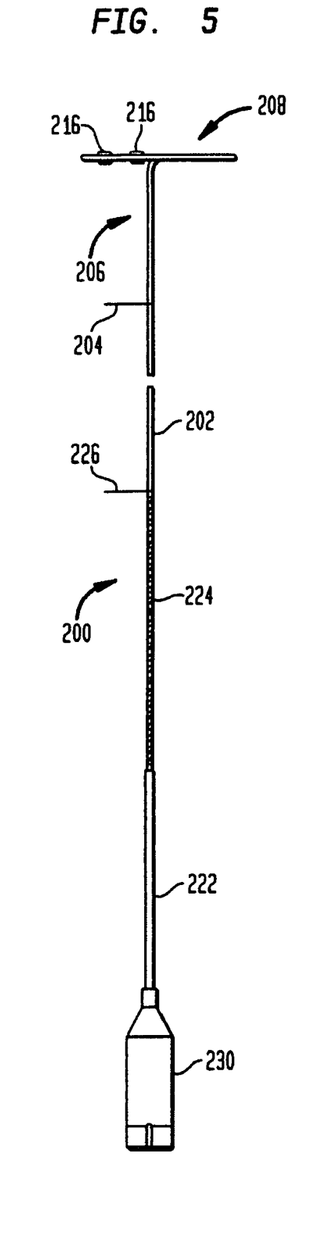
FIG. 5 is a diagrammatic elevational view of a probe in accordance with a second embodiment of the invention.
Figures 6, 7, 8:
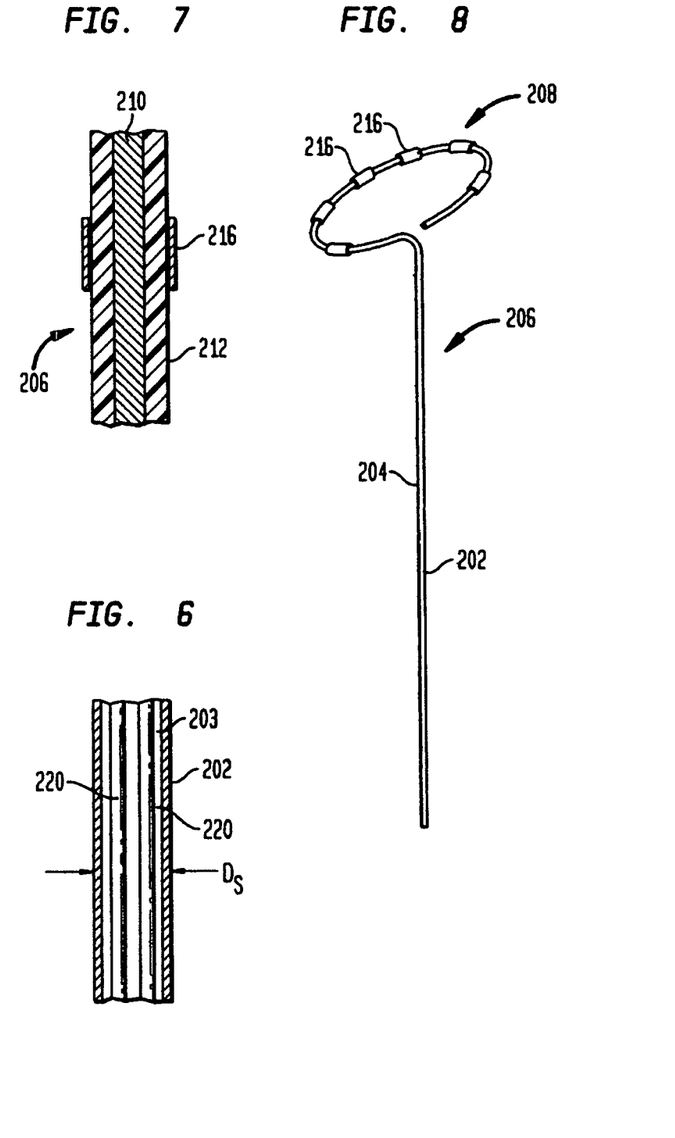
FIG. 6 is a fragmentary diagrammatic sectional view depicting a portion of the probe shown in FIG. 5.
FIG. 7 is a fragmentary diagrammatic sectional view depicting a further portion of the probe shown in FIG. 5.
FIG. 8 is a diagrammatic perspective view depicting a portion of the probe shown in FIG. 5.

A sensor probe in accordance with a second embodiment of the invention has a composite body 200 (FIG. 5) including a tubular metallic shaft section 202 which may be formed from a stainless steel tube of the type commonly used to form hypodermic needles. Shaft section 202 defines an interior bore 203 (FIG. 6). Desirably, shaft section 202 has an outside diameter $D_S$ (FIG. 6) on the order of 1.25 mm or less, more desirably about 1 mm (0.040 inches) or less, and most preferably about 0.9 mm (0.035 inches). Preferably, shaft section 202 extends throughout the majority of the length of probe 200. For example, shaft section 202 may be on the order of 140 cm (55 inches) long.

A distal section 206 is mounted to the distal end 204 of shaft section 202. Distal section 206 includes a wire core 210 (FIG. 7) with a dielectric, biologically inert polymeric covering 212 overlying the core. The core desirably is formed from a metal such as a nickel-titanium alloy which can be formed to a preselected shape and which will tend to return to the preselected shape when unconstrained. A plurality of electrodes 216 overlie covering 212 in a portion of the length of distal section 206. As best seen in FIG. 8, this portion 208 of distal section 206 in its free or unconstrained condition forms a hoop lying in a plane transverse to the axis defined by the remainder of distal section 206. In the free or unconstrained condition, distal 206 section may extend about 5 cm (2 inches) proximally from the plane of the hoop. Distal section 206 is formed to this hoop shape and tends to return to this shape when distal section 206 is unconstrained. However, distal section 206 is quite flexible, and hence, can be constrained to a straight or gently curving shape, so as to be advanced through the passageway defined by the catheters and ablation devices discussed above. Shaft section 202 is flexible enough to pass through gently curving portions of the catheter but is considerably stiffer than distal section 206.

Figure 10:
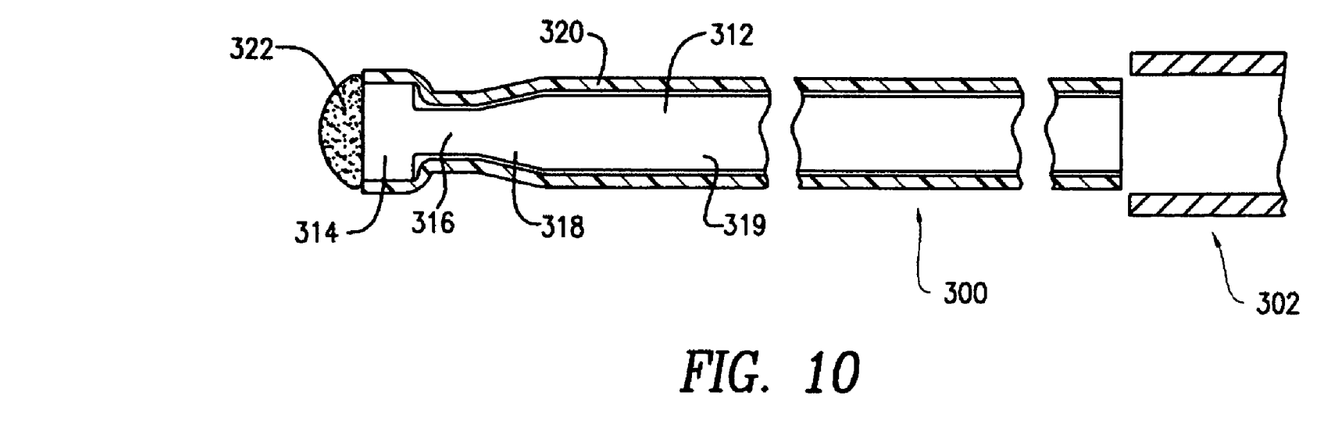
FIG. 10 is a schematic view of the atraumatic tip of the third embodiment.

The proximal end of distal section 206 abuts distal end 204 of shaft section 202 and is bonded to shaft section 202. Desirably, wire core 210 extends into bore 203 of shaft section 202 a short distance from this abut joint. A plurality of fine insulated wires 220 are disposed within bore 203 of shaft section 202. These wires 220 are electrically connected to electrodes 216 on distal section 206. The probe body also includes a proximal section 222 and a transition section 224 extending from proximal section 222 to proximal end 226 of shaft section 202. The proximal end section may include a relatively stiff polymeric tube having an interior bore (not shown). Transition section 224 may include a polymeric tube having stiffness intermediate between that of the proximal end section and shaft section 202, this tube also having an interior bore. The interior bores of the transition section 224 and proximal section 222 may communicate with the bore of shaft section 202. Alternatively, the metallic tube forming shaft section 202 may extend through the interior bores of transition section 224 and proximal section 222. In either arrangement, wires 220 may extend all the way to the proximal end of proximal end section 222. An electrical connector 230 is connected to these wires and, hence, to electrodes 216. An atraumatic tip may be formed at the end region of distal section 206. The details of construction of the atraumatic tip are shown in FIG. 10 and discussed in detail hereafter. In a variation of the second embodiment, distal section 206 may have the shape described in detail hereafter and depicted in FIGS. 11 and 12.

Figure 9:
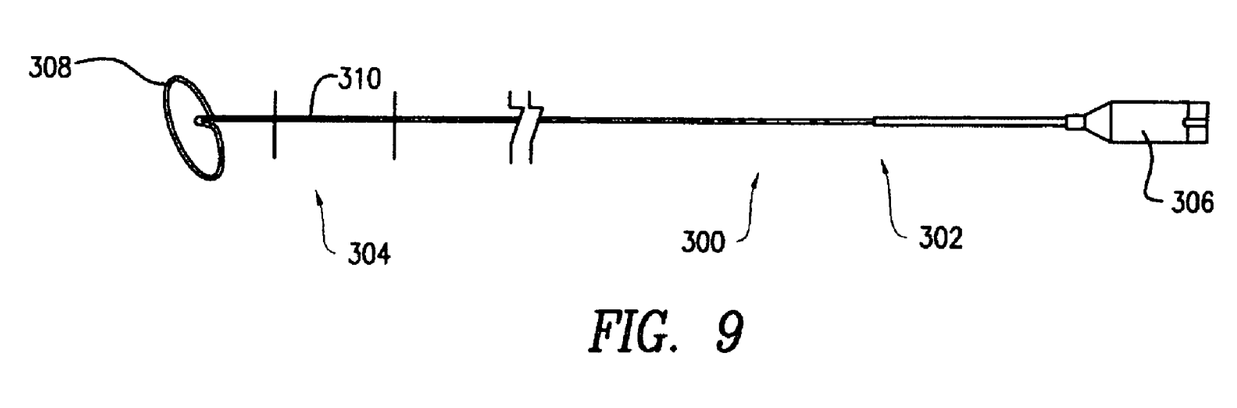
FIG. 9 is a diagrammatic elevational view of a probe in accordance with a third embodiment of the invention.
Figure 11:
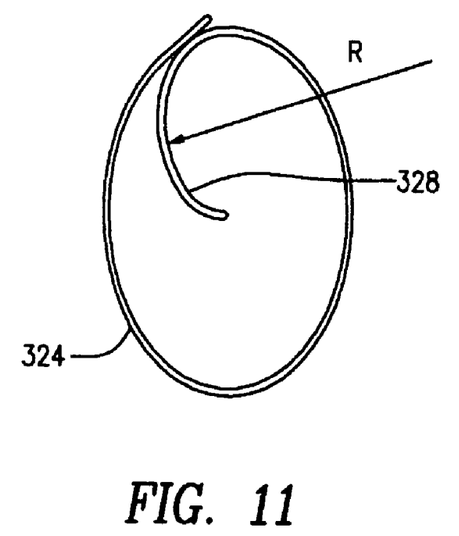
FIG. 11 shows an elevational view of the hoop region of the third embodiment.
Figure 12:
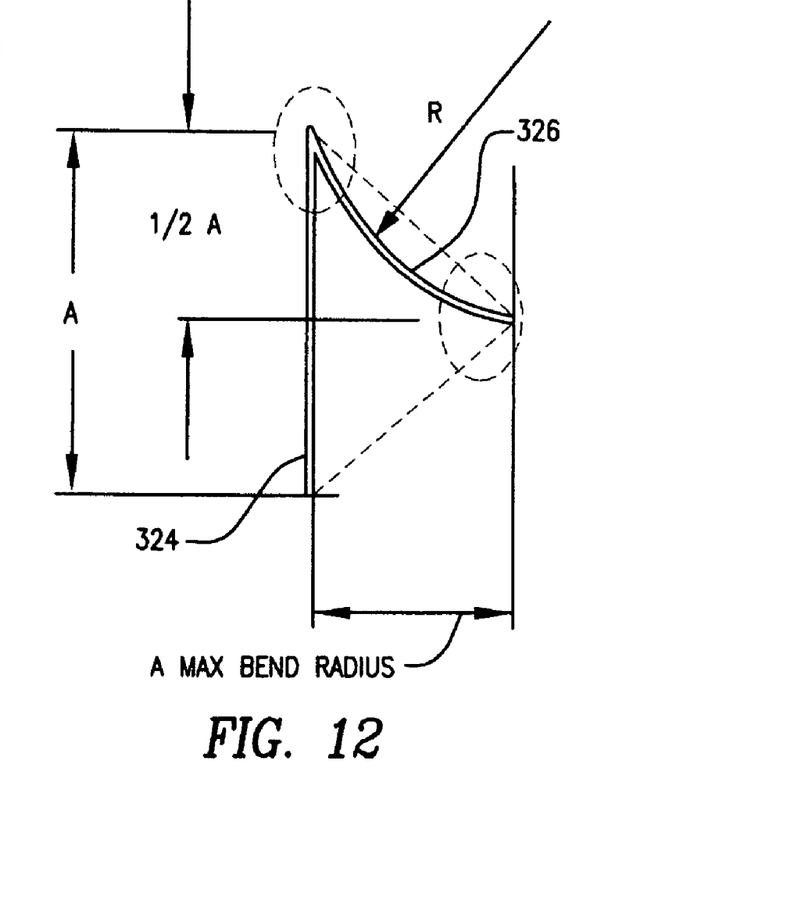
FIG. 12 shows a side view of the hoop region of the third embodiment.

A sensor probe 300 in accordance with a third embodiment of the invention is shown in FIG. 9. Sensor probe 300 has a proximal section 302 and a distal section 304. Proximal section 302 is approximately 90 percent of the length of sensor probe 300. Proximal section 302 includes a stainless steel hypotube coated with Teflon. The stainless steel hypotube provides pushability to the sensor probe 300 and transfers maximum force from a handle 306 to the opposite end of sensor probe 300. A core wire (not shown) runs through the proximal twelve inches of the hypotube to prevent it from collapsing during procedural manipulation. A plurality of electrodes (not shown) extend around a portion of a nitinol wire 312 (FIG. 10) that forms a loop 324 (FIG. 11). The electrodes are electrically insulated from nitinol wire 312. One example of a manner in which the electrodes may be insulated from nitinol wire 312 may be seen in FIG. 3 where the nitinol wire is designated by numeral 94. As seen in FIG.

3 insulated wires 92 are routed along probe body 78 through the dielectric layer 90 and exit dielectric layer 90 through small holes (not shown) cut into dielectric layer 90. The insulation is removed from the portion of the insulated wire 92 extending out from dielectric layer 90. The exposed wire is wrapped around probe body 78 and knotted, providing for a secure connection to probe body 78. A slightly oversized electrode made from Platinum or Pt10Ir is positioned directly over the wrapped wire then is mechanically swaged into position so that it becomes immovable and provides a seal to prevent blood leakage into probe body 78. The electrodes are wired to an electrical connector (not shown) that may be located in handle 306.

Distal section 304 consists of a loop section 308 and an intermediate section 310. Intermediate section 310 includes a polyimide shaft that is approximately 10.5 centimeters long. The polyimide shaft is resistant to compression and at the same time flexible. The polyimide shaft when pushed through a narrow pathway does not increase frictional resistance. The polyimide shaft is connected to the distal end of the hypotube and the proximal end of loop section 308. The soft Pebax® tubing 320 (FIG. 10) and Polyimide tubing are bonded using a lap joint design. The distal end of the Polyimide tubing may be hot necked to accept Pebax® tubing 320. Pebax® tubing 320 is also necked to thin out the wall. The necked length of Pebax® tube 320 is cut to 5 mm. The necked length of the Polyimide tubing is cut to 7 mm. The dies used to neck each tube are configured to enable the necked Pebax® tube 320 to slip fit over the necked section of the Polyimide. Pebax® tubing 320 is slipped over the necked part of the Polyimide and this is heat bonded. This heat bonding process is accomplished in two steps using a progressively tighter Teflon sleeve to ensure a strong bond and to reduce the profile of the bond to match the tubing. The proximal portion of the Polyimide is bonded to the hypotube by first inserting it over a tubing to give it an appropriate shape and thereafter inserting the shaped polyimide tubing over the wire bundle. The part over the wire bundle is inserted into the actual hypotube and heated again to mold the joint. Then, this joint is adhesive bonded by applying cyanoacrylate adhesive (marketed by Locktite corporation) between the hypotube and the molded polyimide to form a lap joint. The Pebax® tube 320 is of a very soft durometer. For example, Pebax® tube may have durometer range of 35-72 shore D. More preferably, the Pebax® tube may have 70 shore D durometer value that allows for maximum flexibility and shapes nicely over the narrow loop radii to create a soft atraumatic tip as discussed hereafter. A single piece of Pebax tubing may be used to make the distal soft segment spanning from the proximal end bonded to the Polyimide shaft and ending at the distal end where it is fused to the ball section 314 of the nitinol wire 312.

FIG. 10 highlights the details of the atraumatic tip of loop section 308 of sensor probe 300. The core section has nitinol wire 312 having a diameter of approximately 0.012 inch. The distal end portion of nitinol wire 312 has four sections—a ball section 314, a reduced section 316, a tapered section 318 and a main section 319. Ball section 314 is the distal most section and is approximately 0.04 inch long. In this section the diameter of the nitinol wire is approximately 0.012 inch. Reduced section 316 is located between ball section 314 and tapered section 318. Reduced section 316 is approximately 0.12 inch in length and approximately 0.005 inch diameter. One end of tapered section 318 is connected to reduced section 316 and has a diameter equal to the reduced section 316 where they are connected. The opposing end of tapered section 318 has larger diameter equal to the diameter of main section 319 and is connected with main section 319. The diameter of the main section is 0.012 inches. A Pebax® tubing 320 covers nitinol wire 312 in distal section 308. Approximately six millimeters of Pebax® tubing 320 covering the distal end portion of nitinol wire 312 is heated in place around nitinol wire 312 at 250° F. for 30 seconds resulting in heat setting in this section. The tubing near the ball section 314 is bonded/melted at 450 deg F. for about 10-15 seconds. This results in Pebax® tubing shrinking in onto the nitinol wire 312 and taking the shape of the underlying nitinol wire 312. The Pebax® tubing physically locks to nitinol wire 312 at reduced section 316, ball section 314 and tapered section 318. Moreover, the Pebax® tubing shrinks into tight frictional engagement with main section 319. The fusing of nitinol wire 312 and Pebax® tubing locks nitinol wire 312 in place relative to the Pebax® tubing and results in a unitized construction. Such construction creates a relatively stable structure that precludes independent movement of outer layers with respect to inner nitinol wire 312 and thereby allows the sensor probe to easily pass through a tight bore. A ball 322 is formed at the very distal tip of ball section 314. Ball 322 is formed from a UV cured adhesive such as Dymax 206-CTH-T, Dymax 203A-CTH-T, or Loctite 3311. Loop section 308 may be formed to loop shape by heat setting in one of the last steps of the assembly procedure. The ball 322 along with the taper formed Pebax® tubing 320 and tapered nitinol wire 312 provide a highly atraumatic tip. An atraumatic tip described above may also be provided for the sensor probes shown in FIGS. 2 and 5 and described in detail previously.

Loop section 308 has loop 324 (FIG. 11). Loop 324 is formed by nitinol wire 312 arcuately bending the wire 312 in two planes perpendicular to each other. Loop 324 lies in a plane perpendicular to the longitudinal axis of nitinol wire 312. To form loop 324, the distal portion of nitinol wire 312 starts to turn away from the longitudinal axis in an arcuate manner. The radius of an arc 326 formed by nitinol wire 312 and as projected in a plane is equal to the diameter of loop 324. The plane on which arc 326 is projected passes through the center of loop 324, runs along the longitudinal axis and is angularly located with respect to loop 324 such that the measured radius is maximum it can be. Upon reaching the plane in which loop 324 is to lay, nitinol wire 312 bends to form loop 324. The diameter of loop 324 may vary between 15 and 25 millimeters. Smaller or larger loop diameter may also be employed. Nitinol wire 312, in forming loop 312, also bends arcuately as projected in the plane of loop 324. The radius of arc 328 may be approximately between 5 and 7 millimeters. The radius of arc 328 is one fourth of the diameter of loop 324. The straight part of the tip is approximately 0.197 inch long and forms the atraumatic tip. The point where the maximum loop diameter is first achieved and the point where the loop ends (i.e., where the atraumatic tip is attached to the loop) form a 30 degree angle with respect to the centre of the loop as seen in end view of loop 324. The end of arc 328 that is at the center of loop 324 is projecting radially out from the center of loop 324. The end of arc 328 that is at the circumference of loop 324 is tangential to loop 324. The tip of nitinol wire 312 turns slightly more than 360 degrees thereby forming a slight overlap in loop 324. The overlap is approximately 0.197 inches. The radius of arcs 326 and 328 are such that the loop structure is compact, sufficiently stiff to hold circular shape during use, but nonetheless capable of being straightened such that the sensor probe can pass through a lumen as small as 0.038 inches or smaller.

In a method according to one aspect of the present invention, ablation device 18 is positioned within a chamber of the heart as, for example, within the left atrium LA of a subject to be treated. A guide sheath (not shown) is advanced through the venous system into the right atrium and through the septum separating the right atrium and left atrium, so that the guide sheath provides access to the left atrium. Typically, the apparatus is advanced through the guide sheath with balloons 20 and 22 in a deflated, collapsed condition. This operation may be performed by first advancing a guide wire (not shown) into the heart, and then advancing insertable structure 10, with balloons 20 and 22 in a deflated condition, over the guide wire, and through the guide sheath. During this operation, probe 72 is not present in tube bore 28 and lumen 30. The guide wire passes through tube bore 28 and through lumen 30. A guide sheath also may be used during the insertion process.

When ablation device 18 is disposed inside the heart chamber, the physician manipulates device 18 to vary the orientation of ablation device 18, and hence the orientation of forward-to-rearward axis 26, until device 18 is positioned in the desired spatial relationship to the heart, with axis 26 extending generally normal to the surface of the heart surrounding the ostium OS of a pulmonary vein PV.

The physician may verify the proper disposition of ablation device 18 relative to the heart by injecting a fluid contrast medium through the continuous passageway defined by lumen 30 and tube bore 28 and out through port 29 on the distal or forward side of ablation device 18. Depending upon the pressure with which the contrast medium is injected, some portion of the contrast medium may pass into the pulmonary vein and other portions may remain within the left atrium. While the contrast medium is present, the subject is imaged using an imaging modality which will show the contrast medium as, for example, conventional x-ray or fluoroscopic imaging.

With the ablation apparatus properly positioned for ablation, the physician may actuate ultrasonic emitter 23, as by actuating an electrical energy source (not shown) connected to emitter 23 by conductors in catheter 12 (also not shown). Ultrasonic emitter 23 directs ultrasonic energy onto wall 24 between balloons 20 and 22, where the energy is reflected in a forward direction F and focused into the ring-like ablation region A. The focused ultrasonic energy heats and ablates the myocardial tissue in this region, thereby converting this tissue into scar tissue which is not capable of conducting electrical impulses.

The physician may detect electrical signals within the pulmonary vein or pulmonary vein ostium by inserting a sensor probe into the subject through the continuous passageway defined by lumen 30 and tube bore 28. Any one of the sensor probes described previously may be used. A method of using the sensor probes is described hereafter with reference to sensor probe shown in FIG. 2, however, the method is also applicable to the sensor probes shown in FIGS. 5 and 9 and any variations thereof. When using the sensor probe of FIG. 2 the physician manually straightens the hoop region and transition portion 84 as these are inserted through the proximal end of the catheter. The probe body 78 has sufficient flexibility so that it can be advanced distally through the passageway. As the probe body 78 advances through catheter 12, the curvature of probe body 78 conforms to the existing curvature of catheter 12. As probe body 78 continues to advance, it reaches the condition shown in FIG. 2. The probe does not tend to buckle and jam as it is threaded through the passageway of the catheter. During threading, of course, the distal end portion is not in the hoop-shape shown, but instead is straight or slightly curved to match the curvature of the passageway in the catheter. As the physician continues to advance the sensor probe 72, the hoop region, distal end 76, and transition region pass distally out of port 26, the atraumatic tip leads the way. Since the atraumatic tip is the part of the hoop region that first contacts tissue, any potential tissue damage such as perforation of heart wall due to being poked by a sharp edge is prevented. Upon exiting port 26, the hoop region and transition region spring back to their unconstrained or deployed shape, as depicted in FIG. 4. This places hoop 82 concentric with axis 96 defined by main region 86 of probe body 78. However, because main region 86 is disposed within tube bore 28 of ablation device 18, main region 86 is coaxial with axis 26 of ablation device 18. Thus, hoop 82 tends to deploy in a plane perpendicular to axis 26 of the ablation device, with hoop 82 concentric with axis 26. As mentioned above, during placement of ablation device 18, the physician has already positioned this axis 26 in alignment with the pulmonary vein ostium and has positioned this axis 26 generally normal to the plane of the heart tissue encircling the ostium. Thus, hoop 82 tends to deploy in a location as shown in FIG. 1, with hoop 82 lodged within the pulmonary vein ostium, or (depending upon the diameter of the pulmonary vein) in the pulmonary vein itself, and with hoop 82 lying in the plane transverse to the axis of the pulmonary vein and the axis of the pulmonary vein ostium. All of this is accomplished without substantial manipulation by the physician to aim or locate hoop 82. Stated another way, ablation device 18 and catheter 12 act as an introducer structure which directs the distal portion of sensor probe 72 into alignment with the pulmonary vein ostium. Thus, placement of sensor probe 72 can be accomplished readily.

Although catheter 12 and ablation device 18 act to introduce and aim the hoop region of the sensor, the hoop region is not rigidly mounted to ablation device 18 or catheter 12, and hence, is not rigidly positioned by these devices. Transition region has some flexibility, so that hoop 82 can be displaced or tilted somewhat from perfect coaxial alignment with ablation device 18. This allows the hoop region to engage the tissues substantially around the pulmonary vein or ostium, even where these anatomical features are not perfectly aligned with the axis of ablation device 18. Also, hoop 82 has some flexibility, and accordingly can conform to these structures, even where the same are not perfectly circular.

With hoop 82 engaged with the tissues, electrodes 80 on hoop 82 will also be engaged with the tissues and hence will receive electrical signals propagating within the tissues. The physician can monitor these electrical signals using a conventional signal detection system 99 (FIG. 1) connected to a connector 88 and hence connected to electrodes 80 through conductors 92 (FIG. 3) of sensor probe 72. If these electrical signals indicate that abnormal conduction is continuing to occur, the physician can actuate the ablation device again. Sensing probe 72 need not be removed from the device during such further ablation. Alternatively, sensing probe 72 may be removed and other procedures, such as injection of additional contrast medium to confirm the desired disposition of ablation device 18, may be performed. In a further variant, sensor probe 72 may be introduced and placed as described above before actuation of ablation device 18, most typically after correct placement of ablation device 18 has been confirmed, as by use of the contrast medium technique discussed above.

In a further variant, ablation device 18 can be repositioned to a new position as partially depicted in broken lines at 18' in FIG. 1. Sensor probe 72 may be retracted into catheter 12 and ablation device 18, or may be entirely removed during the repositioning step. The same steps as discussed above may be repeated. The ability to retract or entirely remove sensor probe 72 facilitates repositioning. For example, contrast medium may be injected again to confirm the moved position of the apparatus. Also, because sensor probe 72 does not project from the apparatus during the repositioning step, it does not interfere with repositioning.

Numerous variations and combinations of the features discussed above can be utilized without departing from the present invention. The probe and method of probe deployment discussed above may be used for purposes other than sensing electrical signals in the context of an ablation process. For example, the probe can be used in a cardiac mapping operation, distinct from an ablation process. In a further variant, the functional elements of the probe (the sensing electrodes) may be used as ablation electrodes; or may be replaced by functional elements other than electrodes as, for example, discrete ultrasonic transducers or the like for an ablation process; or by sensors other than electrodes as, for example, chemical sensors. Further, although the present invention is particularly useful in performing procedures within the heart, it can be applied to performing procedures within other internal organs of a human or animal subject, or indeed, to performing procedures within a cavity of an inanimate subject.

The invention claimed is:

1. Apparatus for cardiac treatment comprising:
   (a) a catheter having proximal and distal ends;
   (b) an expansible ablation device mounted to the catheter at or adjacent the distal end thereof, the ablation device having a lumen therein and a port at a distal end of the lumen;
   (c) an elongated sensor probe having proximal and distal ends, the sensor probe including one or more electrodes disposed adjacent the distal end of the sensor probe, the sensor probe being disposed in the lumen so that the sensor probe can be removably positioned in the lumen with the distal end of the sensor probe projecting out of the ablation device through the port;
   (d) a ball formed at the tip of the distal end of the sensor probe; and
   (e) a floppy section attached to the ball, the floppy section having a wire core and a polymeric tube covering the wire core, the polymeric tube being made from a soft material having a low durometer value and the wire and the polymeric tube being in engagement such that there is no relative motion between them in the area near the ball;
   wherein the floppy section further comprises:
   a ball section formed in the wire, the ball section being attached to the ball;
   a reduced section formed in the wire, the reduced section being attached to the ball section; and
   a tapered section formed in the wire, the tapered section having a small end and a large end, the small end being attached to the reduced section, wherein
   the polymeric tube conforms to the shape of the ball, reduced and tapered sections.

2. The apparatus of claim 1, wherein the wire is made of nitinol.

3. The apparatus of claim 2, wherein the polymeric tube is made of Pebax®.

4. The apparatus of claim 3, wherein the ball is made from UV curable adhesive.

5. The apparatus of claim 4, wherein the UV curable adhesive is chosen from a group consisting of Dymax 206-CTH-T, Dymax 203A-CTH-T and Loctite 3311.

6. Apparatus as claimed in claim 1, wherein the sensor probe includes a tubular metallic shaft section, the sensor probe further including one or more conductors electrically connected to the one or more electrodes, portions of the conductors extending within the shaft section.

7. Apparatus as claimed in claim 6, wherein the distal end section of the sensor probe includes a wire core, the polymeric tube overlying the wire core, the one or more electrodes overlying the polymeric tube so that said tube insulates at least some of the electrodes from the wire core.

8. A sensor probe comprising:
   a probe having a proximal end and a distal end;
   a ball at the tip of the distal end;
   a floppy section attached to the ball, the floppy section having a wire core and a polymeric tube covering the wire core, the polymeric tube being made from a soft material having a low durometer value and the wire core and the polymeric tube being in engagement such that there is no relative motion between them in the area near the ball;
   wherein the floppy section further comprises:
   a ball section formed in the wire, the ball section being attached to the ball;
   a reduced section formed in the wire, the reduced section being attached to the ball section; and
   a tapered section formed in the wire, the tapered section having a small end and a large end, the small end being attached to the reduced section, wherein
   the polymeric tube conforms to the shape of the ball, reduced and tapered sections.

9. The sensor probe of claim 8, wherein the wire is made of a shape-memory alloy.

10. The sensor probe of claim 9, wherein the polymeric tube is made of Pebax®.

11. The sensor probe of claim 10, wherein the ball is made from UV curable adhesive.

12. The sensor probe of claim 11, wherein the UV curable adhesive is chosen from a group consisting of Dymax 206-CTH-T, Dymax 203A-CTH-T and Loctite 3311.

13. The sensor probe of claim 9, further comprising:
   (a) an elongated tubular metallic shaft section having proximal and distal ends;
   (b) a distal section having proximal and distal ends including the wire core and a polymeric tube overlying said wire core, the one or more electrodes overlying said polymeric tube, the distal section being hoop shaped when unconstrained, and at least a part of said distal section having the one or more electrodes thereon; and
   (c) one or more electrical conductors extending within the shaft section, the electrical conductors being electrically connected to the electrodes.

14. A probe as claimed in claim 13, wherein the shaft section and the distal section have cross-sectional dimensions of about 1.00 mm or less.

15. A probe as claimed in claim 14, wherein the one or more electrodes include a plurality of electrodes.

16. A probe as claimed in claim 13, wherein the distal section is substantially more flexible than said shaft section.

17. A sensor probe comprising:
   a catheter having a proximal end and a distal end, the distal end when unconstrained forming a circular loop and an arcuate stem attached to the circumference of the loop, the arcuate stem having a maximum first radius about same size as the diameter of the loop and a minimum second radius equal to about one fourth of the diameter of the loop, wherein:
   the first radius is measured by projecting the stem in a plane that is perpendicular to the plane of the loop and the second radius is measured by projecting the stem in the plane of the loop; and
   the radius of circular loop is in a range of 15 millimeters to 25 millimeters.

18. The sensor probe of claim 17, further comprising:
a ball formed at the tip of the distal end;
a floppy section attached to the ball, the floppy section having a wire core and a polymeric tube covering the wire core, the polymeric tube being made from a soft material having a low durometer value and the wire and the polymeric tube being in engagement such that there is no relative motion between them in the area near the ball.

19. The sensor probe of claim 18, wherein the floppy section further comprises:
a ball section formed in the wire, the ball section being attached to the ball;
a reduced section formed in the wire, the reduced section being attached to the ball section; and
a tapered section formed in the wire, the tapered section having a small end and a large end, the small end being attached to the reduced section, wherein
the polymeric tube conforms to the shape of the ball, reduced and tapered sections.

20. The sensor probe of claim 19, wherein the wire is made of a shape-memory alloy.

21. The sensor probe of claim 20, wherein the outside tube is made of Pebax®.

22. The sensor probe of claim 21, wherein the ball is made from UV curable adhesive.

23. The sensor probe of claim 22, wherein the UV curable adhesive is chosen from a group consisting of Dymax 206-CTH-T, Dymax 203A-CTH-T and Loctite 3311.

24. The sensor probe of claim 20, further comprising:
(a) an elongated tubular metallic shaft section having proximal and distal ends;
(b) a distal section having proximal and distal ends including the wire core and the polymeric tube overlying the wire core, the one or more electrodes overlying the polymeric covering, the distal section being hoop shaped when unconstrained and at least a part of the distal section having the one or more electrodes thereon; and
(c) one or more electrical conductors extending within the shaft section, the electrical conductors being electrically connected to said electrodes.

25. A probe as claimed in claim 24, wherein the shaft section and the distal sections have cross-sectional dimensions of about 1.00 mm or less.

26. A probe as claimed in claim 25, wherein the one or more electrodes include a plurality of electrodes.

27. A probe as claimed in claim 26, wherein said distal section is substantially more flexible than said shaft section.

28. Apparatus for cardiac treatment comprising a sensor probe as claimed in claim 8, a catheter having proximal and distal ends and an expansible ablation device mounted to the catheter at or adjacent the distal end thereof, the ablation device having a lumen therein and a port at a distal end of the lumen, said sensor probe being positionable in the lumen with the distal end of the probe body projecting out of the port.

29. A sensor probe comprising an elongated probe body having proximal and distal ends, said probe body including a main region having electrodes thereon, a floppy region distal to said main region, and a blunt element mounted on said floppy region, said blunt element forming the distal end of the probe body, said floppy region having stiffness in bending less than the stiffness in bending of the main region, wherein the probe body includes a wire core having a main section extending in said main region, a reduced section of lesser diameter than said main section extending in said floppy region, and a tip of greater diameter than said reduced section in said blunt element.

30. A sensor probe as claimed in claim 29 wherein said blunt element is substantially hemispherical.

31. A sensor probe as claimed in claim 29 wherein said probe body further includes a polymeric tube closely surrounding and overlying at least said main section and said reduced section of said wire.

32. A sensor probe as claimed in claim 31 wherein said electrodes are carried on said wire core in said main section, said electrodes being electrically insulated from the wire core by a layer of insulating material located between the electrodes and the wire core.

33. A sensor probe as claimed in claim 31 wherein said polymeric tube also overlies at least a portion of the tip of the wire.

34. A sensor probe as claimed in claim 33 wherein said blunt element includes a polymeric mass adhering to the tip of the wire and the tube.

35. A sensor probe as claimed in claim 29 wherein said wire has a tapered section between said tip and said main section.

36. A sensor probe as claimed in claim 29 wherein said tip has a diameter equal to the diameter of the main section.

37. A sensor probe as claimed in claim 29 wherein, in an unconstrained condition, said main region of said probe body defines a generally straight region extending along an axis, a stem distal to the straight region, the stem extending transverse to the axis, and a loop distal to the stem, the loop lying generally in a plane transverse to the axis of the axially-extending portion and being substantially coaxial with the straight region.

38. A sensor probe as claimed in claim 37 wherein said stem is arcuate.

39. A sensor probe as claimed in claim 38 wherein said stem curves in laterally away from the axis of the straight region and also curves in a circumferential direction around a second axis that is substantially parallel to the axis of the straight region.

40. A sensor probe as claimed in claim 39 wherein the stem curve has a maximum first radius about same size as the diameter of the loop and a minimum second radius equal to about one fourth of the diameter of the loop, wherein
the first radius is measured by projecting the stem in a plane that is perpendicular to the plane of the loop and the second radius is measured by projecting the stem in the plane of the loop.

* * * * *

UNITED STATES PATENT AND TRADEMARK OFFICE
CERTIFICATE OF CORRECTION

PATENT NO. : 7,860,578 B2
APPLICATION NO. : 11/891065
DATED : December 28, 2010
INVENTOR(S) : Jung et al.

Page 1 of 1

It is certified that error appears in the above-identified patent and that said Letters Patent is hereby corrected as shown below:

On the Title Page:

Item No. (75) Inventors: after "Eugene J. Jung", delete "Nesconset", and insert therefor -- Ronkonkoma --.

Signed and Sealed this
Fifteenth Day of February, 2011

David J. Kappos
*Director of the United States Patent and Trademark Office*